United States Patent
Watanabe

[19]

[11] Patent Number: 6,164,133
[45] Date of Patent: Dec. 26, 2000

[54] METHOD AND APPARATUS FOR PRE-PROCESSING OF SEMICONDUCTOR SUBSTRATE SURFACE ANALYSIS

[75] Inventor: Kaori Watanabe, Tokyo, Japan

[73] Assignee: NEC Corporation, Tokyo, Japan

[21] Appl. No.: 09/146,434

[22] Filed: Sep. 3, 1998

[30] Foreign Application Priority Data

Sep. 3, 1997 [JP] Japan ................................. 9-237912

[51] Int. Cl.[7] ...................................................... B08B 3/04
[52] U.S. Cl. ..................... 73/432.1; 73/DIG. 1; 134/1.3; 134/95.1; 134/902; 134/105; 134/155
[58] Field of Search ................. 73/570, 432.1, 73/DIG. 1; 134/1, 1.3, 24, 26, 30, 94.1, 95.1, 95.3, 96.1, 97.1, 105, 107, 108, 902, 153, 151, 154, 155

[56] References Cited

U.S. PATENT DOCUMENTS

| 5,039,349 | 8/1991 | Schoeppel | 134/26 |
| 5,100,476 | 3/1992 | Mase et al. | 134/1 |
| 5,365,960 | 11/1994 | Bran | 134/184 |
| 5,487,398 | 1/1996 | Ohmi et al. | 134/95.1 |
| 5,733,434 | 3/1998 | Harada et al. | 205/746 |
| 5,872,046 | 2/1999 | Kaeriyama et al. | 438/465 |
| 5,922,136 | 7/1999 | Huang | 134/2 |
| 6,039,814 | 3/2000 | Ohmi et al. | 134/1 |

FOREIGN PATENT DOCUMENTS

| 2-28533 | 1/1990 | Japan . |
| 2-229428 | 9/1990 | Japan . |
| 5-288743 | 11/1993 | Japan . |

Primary Examiner—Hezron Williams
Assistant Examiner—Rose M. Miller
Attorney, Agent, or Firm—Sughrue, Mion, Zinn, Macpeak & Seas, PLLC

[57] ABSTRACT

A semiconductor substrate surface analysis pre-processing apparatus has a substrate section which holds a decomposition/collecting liquid that is caused to come into contact with the entire surface of a substrate to be surface-analyzed, a substrate transport section which holds the substrate to be surface-analyzed, and which moves the substrate between a substrate carrier and the substrate processing section, a supply and ejection means for the decomposition/collecting liquid, and a processing operation means that performs either ultrasonic or heat processing with respect to the substrate processing section.

7 Claims, 8 Drawing Sheets

- 25 SUBSTATE TRANSPORT SECTION
- 20 SEMICONDUCTOR SUBSTRATE
- 22 DECOMPOSITION/COLLECTING LIQUID
- 24 SUBSTRATE PROCESSING SECTION
- 23' 
- 23 ULTRASONIC GENERATOR AND HEATER
- 23"

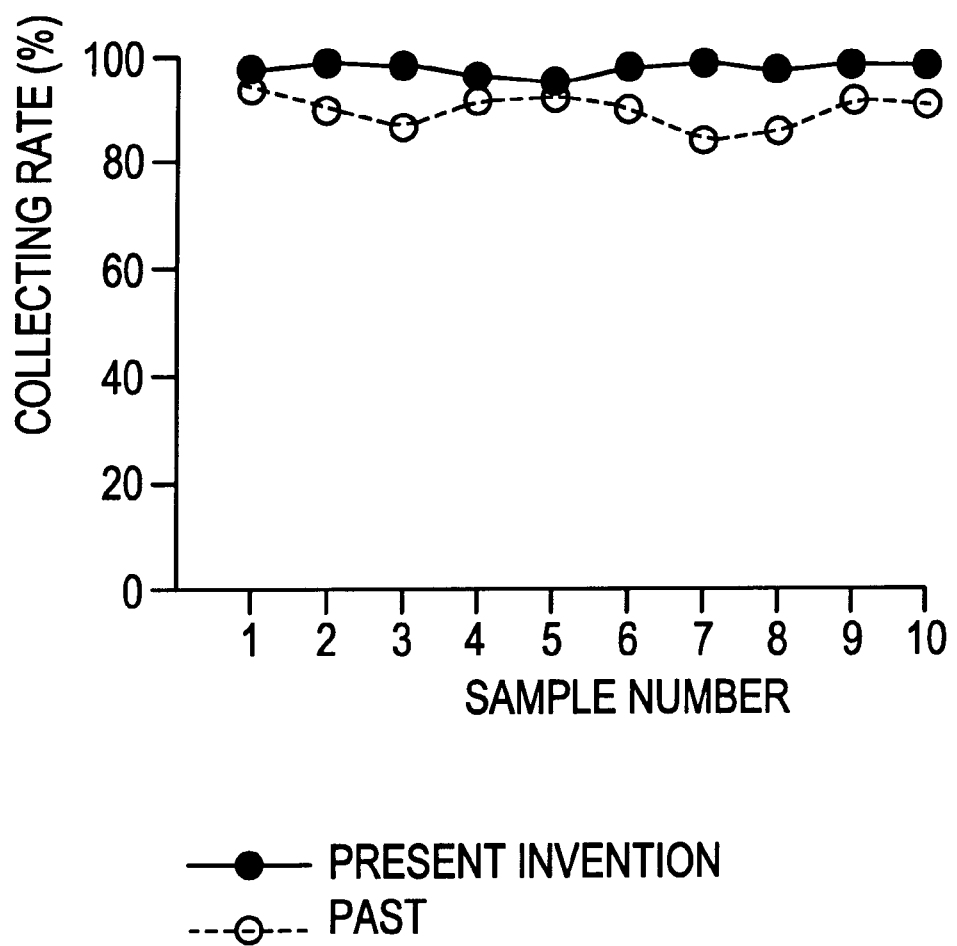

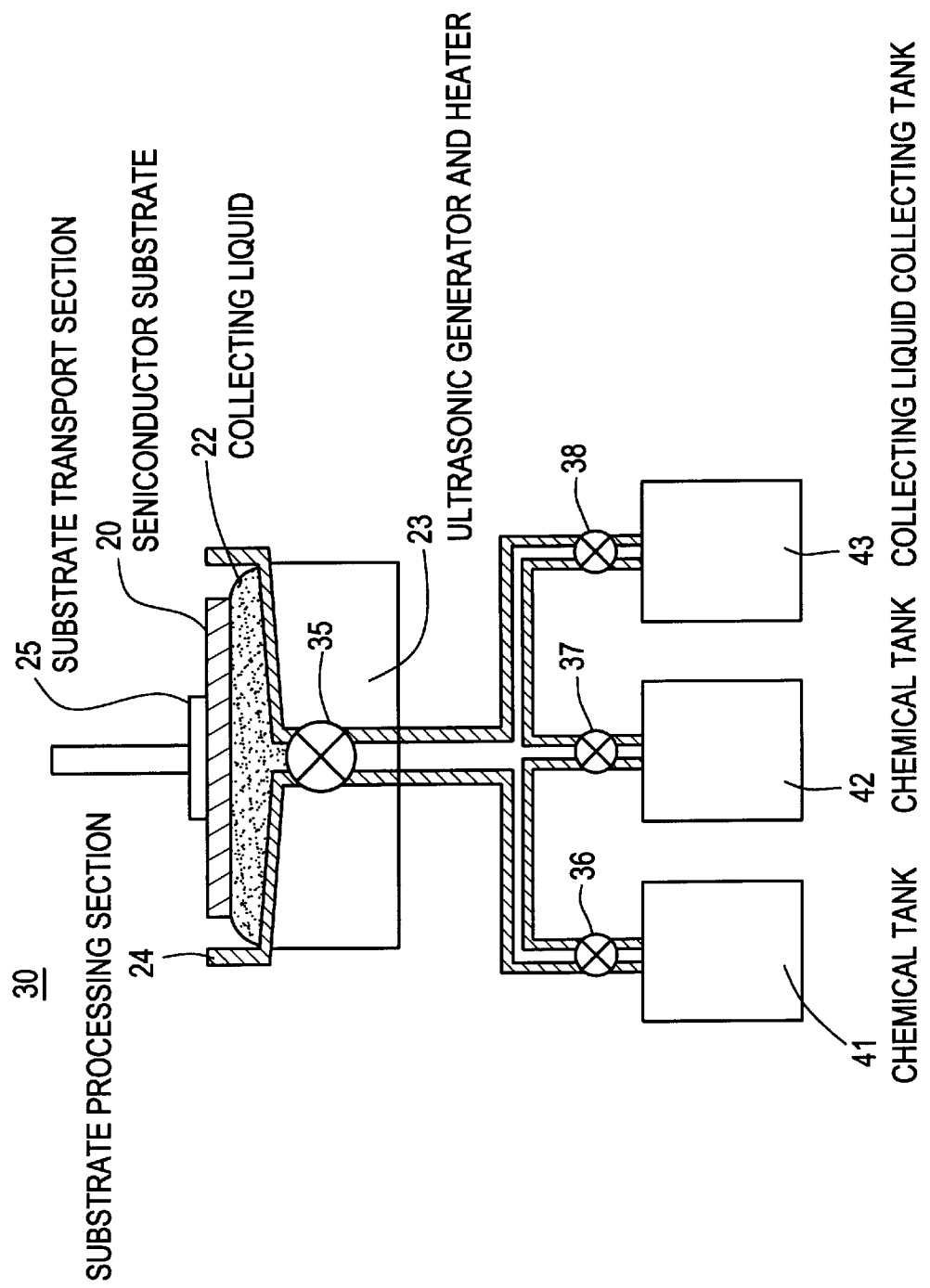

METHOD AND APPARATUS FOR PRE-PROCESSING OF SEMICONDUCTOR SUBSTRATE SURFACE ANALYSIS

BACKGROUND OF THE INVENTION

1. Field of the Invention

The present invention relates to a method and apparatus for pre-processing of semiconductor substrate surface analysis, and more specifically to a method and apparatus for pre-processing for the purpose of analyzing contaminating matter on the surface of a semiconductor substrate.

2. Description of Related Art

In the electronics industry in the past, as devices have become smaller, wafer contamination attributed to materials and impurities generated during necessary operation of processes, and particularly metallic wafer contamination is a problem in terms of causing excessive leakage currents, and deterioration of junction breakdown voltage and oxide film breakdown voltage.

Therefore, for the purpose of achieving higher device reliability and improving production yield, it is necessary to reduce metallic wafer contamination, by achieving high material purity and reducing process contamination. Thus, it is essential to gain a quantitative understanding of the contamination level in manufacturing processes.

In the past, it was said to be necessary to reduce the line contamination level to below $1 \times 10^{10}$ atoms/cm$^2$, and the metallic contamination evaluation technology to analyze this has required a sensitivity of $10^9$ atoms/cm$^2$ or more.

In this metallic contamination impurity analysis method for the surface of a semiconductor silicon substrate, chemical analysis is generally used, such as disclosed in Japanese Unexamined Patent Publication (KOKAI) No. 2-28533, which discloses a hydrofluoric acid VPD-AAS (vapor phase decomposition-atomic absorption spectrometry) method and a hydrofluoric acid VDP-ICP-MS (VDP-ICP-MS: vapor phase decomposition-inductively coupled plasma-mass spectrometry) method.

The pre-processing VPD method which is used, as shown in FIG. 7, is that of heating a hydrofluoric acid solution 15 that is supported in a groove 13 inside a hermetically sealed chamber 10 in which semiconductor wafers are resting on a wafer support stand 11, so that the generated hydrofluoric acid vapor decomposes the native oxide film, an oxide film, and a nitride film and the like on the semiconductor substrate.

Additionally, as shown in FIG. 8(A), according to another example disclosed in the above-noted patent publication, a drop 17 of hydrofluoric acid solution is placed on top of a semiconductor substrate 14 which rests on a wafer support stand 11, the wafer support stand 11, as shown in FIG. 8(B) and FIG. 8(C) being undulated up and down so that the drop 17 of the hydrofluoric acid solution is caused to describe a path as shown in FIG. 8(D) and FIG. 8(F) along the surface of the semiconductor substrate 14, so that this acts as a collecting fluid that collects residual metallic impurities therefrom, the collected collecting fluid in this method being measured by AAS or ICP-MS or the like, thereby enabling analysis that is more sensitive than physical analysis methods such as SIMS (secondary ion mass spectrometry) and TXRF (total reflection X-ray fluorescence).

Additionally, in recent years, as disclosed in the Japanese Unexamined Patent Publication (KOKAI) No. 2-229428, and as shown in FIG. 9(A) and FIG. 9(B), a pre-processing apparatus has been developed that automates the VPD processing.

FIG. 9 shows a treatment liquid collecting apparatus 10 which comprises a vapor phase decomposition system in which a semiconductor substrate 12, which rests on a carrier 5 provided within a container 2 is decomposed by hydrofluoric acid vapor 4 or the like, a semiconductor substrate transport apparatus 7, and an apparatus 9 which supports a semiconductor substrate 12 on a semiconductor substrate support apparatus 6 and which, by means of a dripping means 8, causes a liquid 17 that is supported by a liquid support part 18 to come into contact with the surface of the semiconductor substrate 12, and scans this, after which it collects the drop by the drop collecting means 9, having a plurality of liquid collecting portions 19.

Of the above-described chemical analysis methods of the past, however, with the VPD method such as shown in FIG. 7 and FIG. 8, which is performed manually by a worker, because it is necessary to perform a scan of the entire surface of the substrate with approximately several hundreds (100) $\mu$l of the collecting liquid, the work of scanning the collecting liquid requires that the worker be highly skilled.

In particular in this method, it is difficult to collect impurities around the periphery of the substrate, collecting non-uniformity occurs, and the collecting rate varies between substrates. This presents a problem in performing quantitative analysis.

As the diameters of substrates in the semiconductor industry grow, the larger the substrate size becomes, the larger is the variation in collecting rate, and the larger the collecting time, which leads to atmospheric contamination.

For this reason, although an automatic pre-processing machine has been developed in recent years, several hours are required for substrate surface analysis using hydrofluoric acid vapor, and approximately 10 minutes must be spent on collecting in the case of each 8-inch substrate. As a result of the time required and the fact that it is impossible to scan the entire substrate surface to its periphery with the collecting liquid, this process causes problems of collecting rate and measurement error.

In recent years, because various types of VPD processing collecting decomposition/collecting liquid have come into use, there are various problems, such as unsafe collecting liquids that generate gases and collecting liquids that are hydrophilic on a silicon substrate and therefore difficult to collect.

The present invention can solve these problems.

With regard to substrate surface analysis as in the present invention because of the need to perform quantitative analysis, it is necessary to collect almost 100% of impurities from the surface of a substrate and to collect precisely all of the decomposition/collecting fluid, there has been delay in automating in this field.

An object of the present invention is to provide a pre-processing method for semiconductor substrate analysis which improves on the problems as described above in the prior art, and which uses a simple apparatus to provide highly accurate analysis data by a simply performed analysis.

SUMMARY OF THE INVENTION

To achieve the above-noted object, the present invention has the technical constitution described below.

Specifically, the first aspect of the present invention is a pre-processing method for semiconductor substrate surface analysis whereby, with a decomposition/collecting liquid in a condition of contact the surface of a semiconductor substrate with respect to which surface analysis is to be performed, the decomposition/collecting liquid is subject to either ultrasonic or heat processing.

The second aspect of the present invention is a pre-processing apparatus for semiconductor substrate surface analysis, this apparatus having a substrate processing section that supports a decomposition/collecting liquid that is caused to come into contact with the entire surface of the semiconductor substrate with respect to which surface analysis is to be performed, a substrate transport section which supports the substrate to be surface-analyzed and which moves the substrate to be surface-analyzed between a substrate carrier and the substrate processing section, a supply and ejection apparatus for the decomposition/collecting fluid, and a processing operation section that subjects the substrate processing section to either ultrasonic or heat processing.

A feature of a semiconductor substrate surface analysis pre-processing apparatus and semiconductor substrate surface analysis pre-processing method according to the present invention is that either ultrasonic processing or heating is used with the decomposition/collecting liquid in a condition of contact with the entire surface of the substrate, so that it is possible to perform decomposition collecting at one time over the entire substrate surface in a short period of time.

More specifically, contaminating matter on the surface of a semiconductor substrate is generally attached metals, ions, and particles in many cases, so that by using either an ultrasonic means or heating means, which are widely used and which are effective in removing contaminating matter and impurities by cleaning, in combination with a collecting operation that uses a chemical liquid that is capable of dissolving metals and attached molecules reliably removes contaminating matter and impurities.

BRIEF DESCRIPTION OF THE DRAWINGS

FIG. 3 is a graph which shows comparison data with regard to the collecting rate for a semiconductor substrate surface analysis pre-processing method of the present invention and a pre-processing method of the past.

FIG. 5 is a side view which shows the configuration of another example of a semiconductor substrate surface analysis pre-processing apparatus according to the present invention.

DETAILED DESCRIPTION OF THE PREFERRED EMBODIMENTS

Embodiments of a semiconductor substrate surface analysis pre-processing apparatus and a semiconductor substrate surface analysis pre-processing method according to the present invention are described in detail below, with reference being made to the relevant accompanying drawings.

Figure 1:
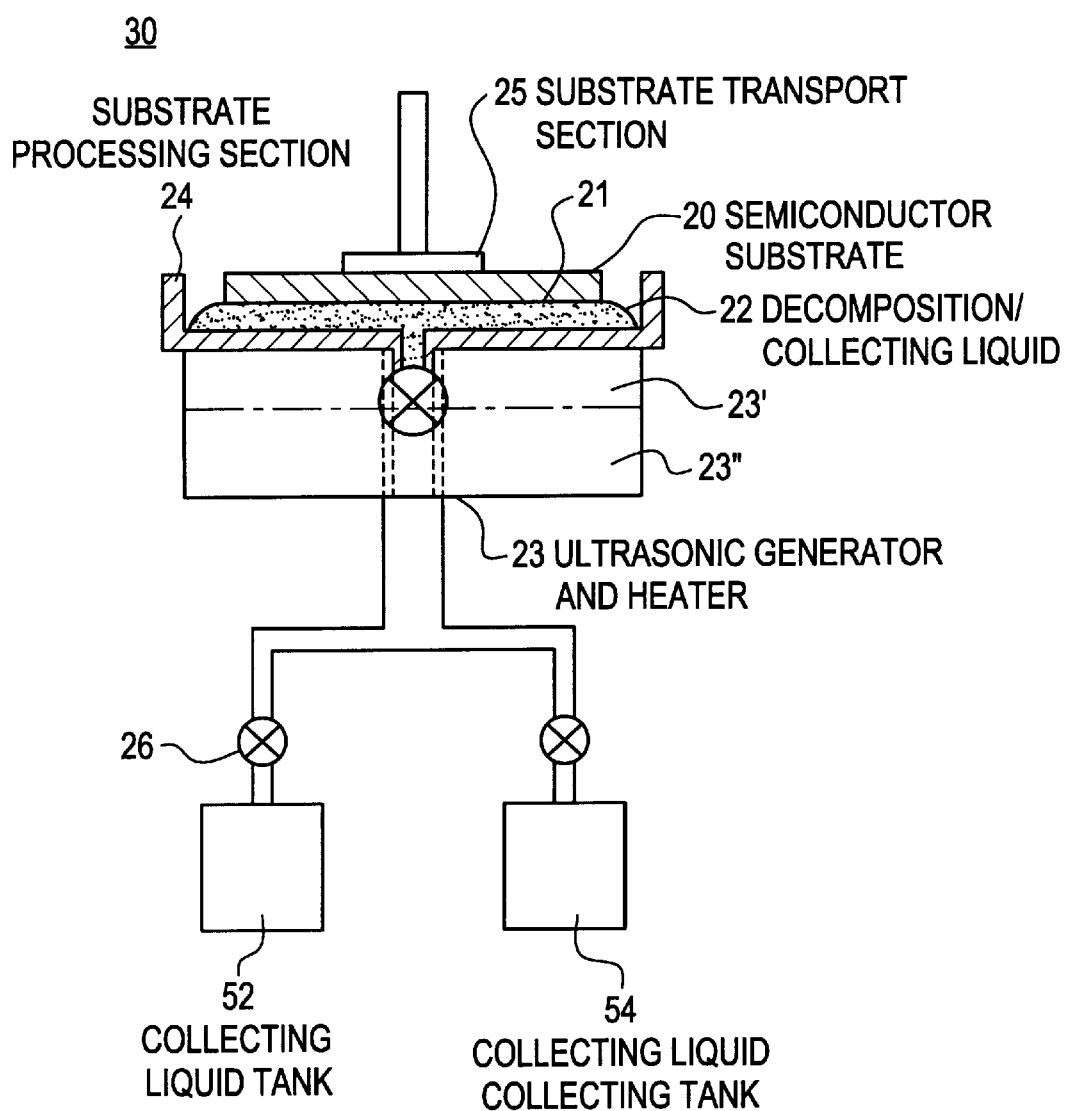
FIG. 1 is a side view which shows the configuration of an example of a semiconductor substrate surface analysis pre-processing apparatus according to the present invention.

Specifically, FIG. 1 is a cross-sectional view which shows the configuration of an example of a semiconductor substrate surface analysis pre-processing apparatus according to the present invention, this drawing showing a semiconductor substrate surface analysis pre-processing apparatus 30 which is provided with a substrate processing section 24, which holds a decomposition/collecting liquid 22 that is caused to come into contact with the entire surface 21 of the substrate 22 to be surface-analyzed, that is, the surface to be inspected, a substrate transport section 25, which holds the substrate 20 for surface analysis, and which performs movement of the substrate 20 for surface analysis between a substrate carrier portion (not shown in the drawing) and the substrate processing section 24, a supply and ejection apparatus 26 for the decomposition/collecting liquid 22, and a processing operation section 23, which subjects the substrate 20 to either ultrasonic or heat processing. A collecting liquid tank 52 is connected to the supply and ejection apparatus 26, and a collecting liquid collecting tank 54 is provided to collect the collecting liquid.

The construction or configuration of the substrate processing section 24 in the present invention is not restricted to any particular shape, and can be any shape that is capable of stably supporting a prescribed amount of the decomposition/collecting liquid. Nor is there a restriction with regard to the material thereof, although the part of the substrate processing section 24 that comes into contact with the decomposition/collecting liquid 22 is preferably made of a fluorine resin or covered by a fluoride resin.

It is desirable that the decomposition/collecting liquid used in surface analysis of a semiconductor substrate in the present invention be at least one dilute aqueous solution or dilute mixture of aqueous solutions selected from the group consisting of pure water, hydrofluoric acid, hydrofluoric acid-hydrogen peroxide solution, hydrofluoric acid-nitric acid, hydrochloric acid-hydrogen peroxide solution, ammonia-hydrogen peroxide solution, sulfuric acid-hydrogen peroxide solution, and hydrochloric acid-nitric acid.

Additionally, in the present invention it is preferable that the decomposition/collecting liquid 22 include a surfactant.

A feature of the present invention is that ultrasonic and heat treating are performed on the decomposition/collecting liquid that is held by substrate processing section 24, and there is no particular restriction with regard to the ultrasonic processing conditions, it being possible to use an arbitrary frequency, nor is there any particular restriction with regard to temperature conditions for heat treating.

Each condition for the above-noted processing operation can be arbitrary established at an optimum condition, respectively, in accordance with the conditions about the decomposition/collecting liquid to be used and the materials to be collected.

In the present invention, it is preferable to perform an operation which uses ultrasonic processing and heat treating together.

A semiconductor substrate surface analysis pre-processing method according to the present invention is described in detail below, with reference being made to the accompanying drawing, using a semiconductor substrate surface analysis pre-processing apparatus according to the present invention.

Specifically, using the apparatus which is shown in FIG. 1, in executing pre-processing of semiconductor substrate surface analysis, a round dish-shaped structure made of a fluororesin of a size that holds the semiconductor substrate 20, for example, is used as the substrate processing section 24 that holds the decomposition/collecting liquid, a semiconductor substrate surface analysis pre-processing apparatus 30 which has both an ultrasonic generator 23' and a heater 23" being used at the bottom part of this dish-shaped substrate processing section 24.

Figure 2A:
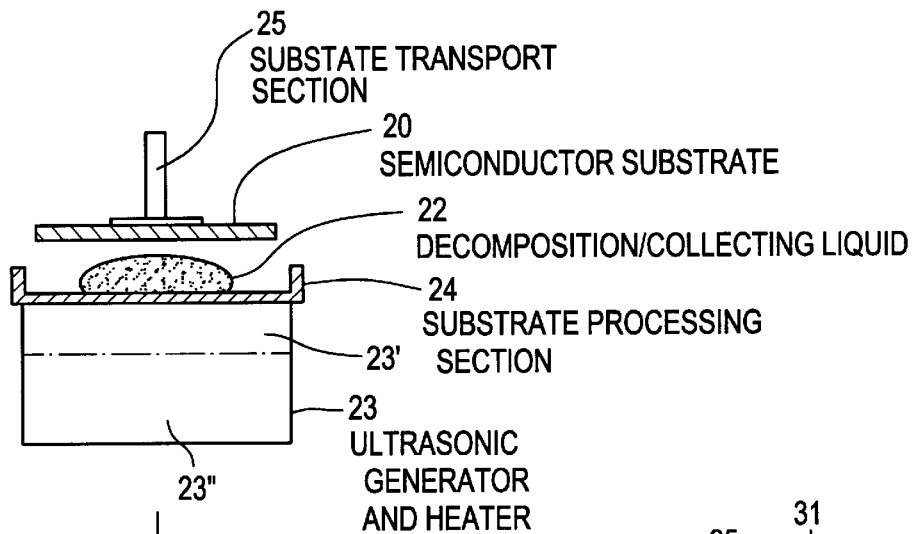
FIG. 2(A) through FIG. 2(E) are side views which show an example of the operation in a semiconductor substrate surface analysis pre-processing method according to the present invention.

First, as shown in FIG. 2(A) through FIG. 2(E), several milliliters, for example, of the decomposition/collecting liquid 22 is dripped onto the dish-shaped substrate processing section 24 made of a fluororesin (FIG. 2(A)).

Then, a substrate transport section 25 that is formed by, for example, a vacuum chuck, and which holds the reverse side of the semiconductor substrate 20 lowers the semiconductor substrate 20 at a low speed with keeping the substrate in a horizontal condition, to a distance such that the collecting liquid does not flow around to the reverse side of the substrate, thereby bringing the surface-analysis surface 21 of the semiconductor substrate 20 into contact with the decomposition/collecting liquid 22.

Figure 2B:
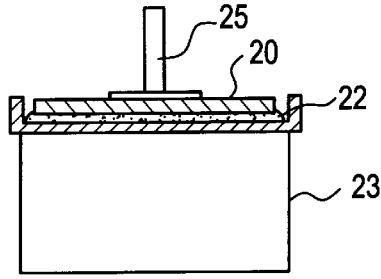

In this condition, ultrasonic processing or heat treating or, if necessary, both are performed simultaneously, so that contaminating matter that is attached one surface 21 of the semiconductor substrate 20 is captured by the collecting liquid 22 (FIG. 2(B)).

After collecting of the impurities or contaminating matter by the decomposition/collecting liquid, the ultrasonic processing operation, the heat treating operation or both are stopped, and the semiconductor substrate 20 is lifted at low speed from an edge 31 thereof.

Figure 2C:
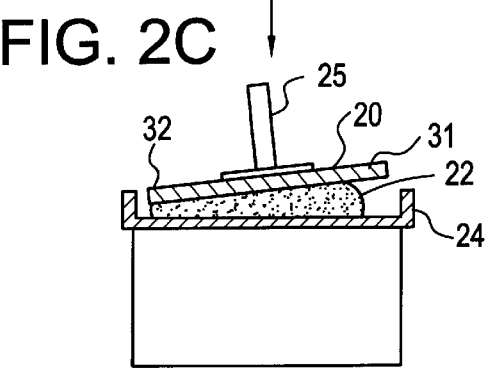
Figure 2D:
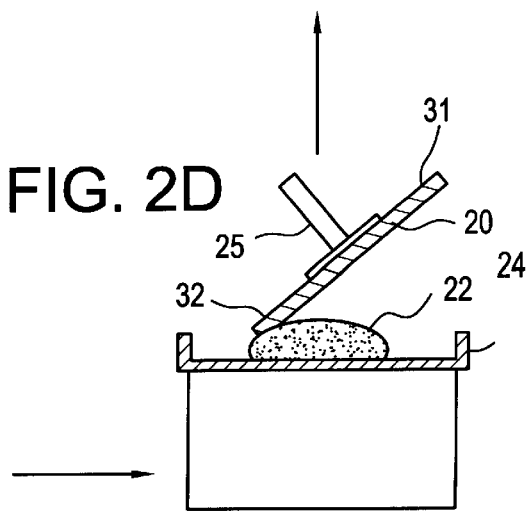
Figure 2E:
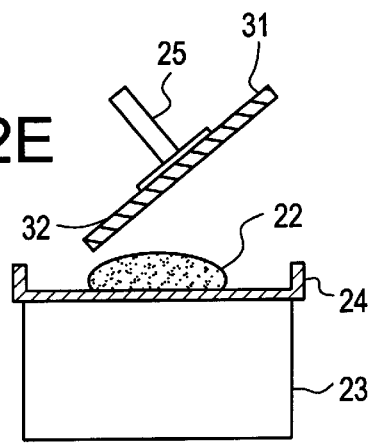

When this is done, as shown in FIG. 2(C) an edge 32 on the other side of the substrate 20 is kept in contact with the collecting liquid 22 and, as shown in FIG. 2(D), the separation angle thereof is gradually increased until, as shown in FIG. 2(E), this part 32 is lifted up.

By doing this, it is possible to clearly remove just the collecting liquid from the surface 21 of the semiconductor substrate, and also possible to completely recover exactly the same amount of decomposition/collecting liquid as was originally dripped.

The above is extremely important, in view of the fact that semiconductor substrate surface analysis which is the purpose of the present invention, is a quantitative analysis.

In the present invention, a concentration measurement is performed on this liquid, using a high-sensitivity metal impurity analyzer, such as an AAS or ICP-MS.

Considering improvement in measurement sensitivity and the adverse influence of concentrated acid on the measurement apparatus, it is better yet to perform the measurement by solving the collecting liquid into a small amount of dilute acid or pure water after it is vaporized and dried.

Using the above-noted semiconductor substrate surface analysis pre-processing apparatus 30 pre-processing is performed, and analysis results are indicated.

Specifically, the processing conditions when employing the above-noted semiconductor substrate surface analysis pre-processing method according to the present invention are as follows.

Using 5 ml of a mixed solution of 1% hydrofluoric acid and 5% hydrogen peroxide as the decomposition/collecting liquid 22, decomposition was done using ultrasonic waves.

The semiconductor substrate 20 is brought to a distance of 2 mm from the bottom surface of the substrate processing section 24, which is formed by a fluororesin dish, and is caused to come into contact with the collecting liquid 22. By doing this, it is possible to cause the collecting liquid to come into contact with the entire surface of the substrate 21.

Decomposition processing is done by ultrasonic waves for 30 seconds. The series of operations can be performed in approximately 1 minute for each substrate 20, regardless of the size of the substrate 20.

After the decomposition/collecting liquid 22 is vaporized and dried, it is dissolved in a 0.7% solution of nitric acid, the concentration of metal in this liquid being measured by ICP-MS.

FIG. 3 shows that results of a comparison experiment, using a substrate in which metal contamination to $1 \times 10^{11}$ atoms/cm$^2$ of iron (Fe) was purposely caused, the comparison being made between the VPD method of the past and the pre-processing method of the present invention, and showing the dispersion in collecting rates for the two methods.

From these results, it can be seen that the pre-processing method of the present invention exhibits less dispersion than the method of the past, and exhibits a higher repeatability of collecting ratio.

Figure 4:
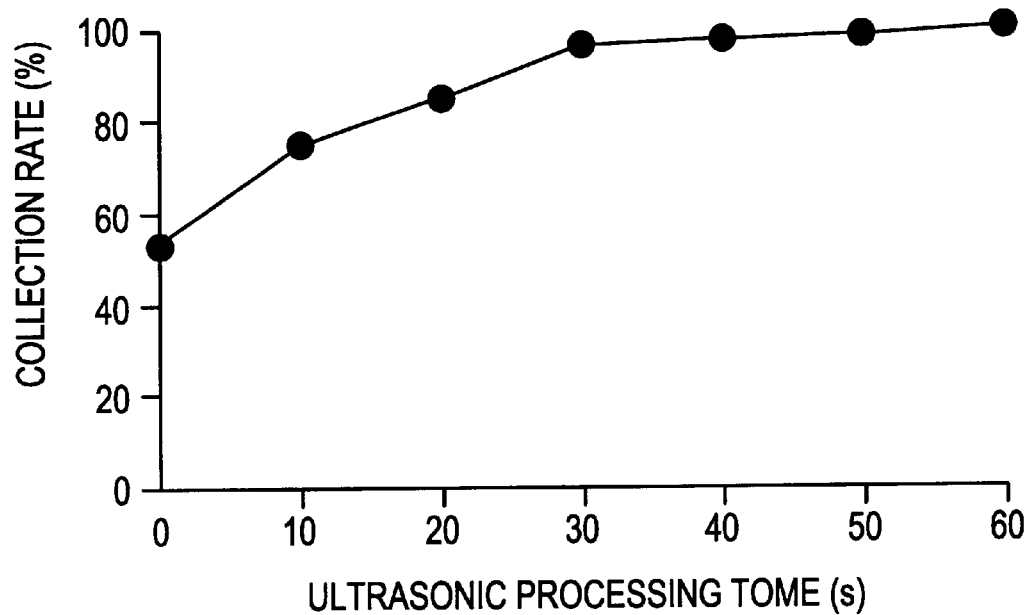
FIG. 4 is a graph which illustrates the effect of ultrasonic processing in a pre-processing method according to the present invention.

FIG. 4 shows the difference in collecting ratio with respect to the ultrasonic energy application time in the pre-processing method of the present invention, using a substrate in which metal contamination to $1 \times 10^{11}$ atoms/cm$^2$ of iron was purposely caused.

From these results, it can be seen that in the case of iron attached to the surface to be collected, there is already 50% collection under a condition in that the collecting liquid being contacted to the substrate, and thereafter a collecting rate of nearly 100% is achieved with an ultrasonic operation time of 30 seconds.

That is, the basic technical concept in a semiconductor substrate surface analysis pre-processing method according to the present invention is that whereby, with the decomposition/collecting liquid in a condition of contact with the entire surface of the substrate to the surface-analyzed, ultrasonic process or heat treating process is done to the decomposition/collecting liquid.

In terms of the apparatus, in addition to the basic semiconductor substrate surface analysis pre-processing apparatus 30 which is shown in FIG. 1, the substrate transport section 25 includes the function of causing the substrate surface 21 to be surface-analyzed to come into contact with the decomposition/collecting liquid 22 and the function of removing the substrate surface 21 from the decomposition/collecting liquid, and also minimally has a function that, when the substrate surface 21 for surface-analysis is removed from the decomposition/collecting liquid 22, removes the substrate in such a manner that the surface of the decomposition/collecting liquid 22 and contact surface of the substrate with the decomposition/collecting liquid intersect.

A second example of the semiconductor substrate surface analysis pre-processing method according to the present invention, this being an example of an automated preprocessing apparatus, is shown in FIG. 5.

In this example of the present invention, by switching of valves 36 and 37, which are provided at the bottom center part of the round substrate processing section 24 made of a fluororesin and which has a slope downward toward the center thereof, the decomposition/collecting liquid 22 is guided from the decomposition/collecting liquid tanks 41 and 42 to the substrate processing section 24.

The collecting liquid tanks are connected to several bottles 41 and 42, which contain various acids, and when this is guided into the substrate processing section, the openings of the valves 35, 36, and 37 are adjusted, so as to provide an arbitrary liquidity and concentration.

From above the collecting liquid 22 that is guided into the substrate processing section 24, the substrate transport section 25, which is provided a vacuum chuck or the like, causing the surface of the substrate 20 which it holds to come into horizontal contact, so that its entire surface is immersed into the collecting liquid.

In this condition, ultrasonic or heat processing is performed with respect to the decomposition/collecting liquid 22, so as to decompose or dissolve the metallic contaminating matter that is attached to the substrate surface, which is then captured in the collecting liquid.

After collecting of the decomposition/collecting liquid 22, the substrate is lifted up at a low speed from one edge 31 thereof, so as to gradually separate it from the decomposition/collecting liquid.

When this is done, an edge 32 on the other side of the substrate 20 is kept in contact with the collecting liquid 22, until finally this part is lifted up.

Thereafter, switching is done from valves 36 and 37 to valve 38, so that the collecting liquid is collected into the collecting liquid collecting tank 43, a concentration measurement being performed on this liquid by means of a high-sensitivity metallic impurity analyzer such as AAS and ICP-MS.

In the third example, an embodiment of the present invention is a further automated pre-processing apparatus. FIG. 6 shows a pre-processing apparatus that features even further automation than that shown in FIG. 5.

Figure 6A:
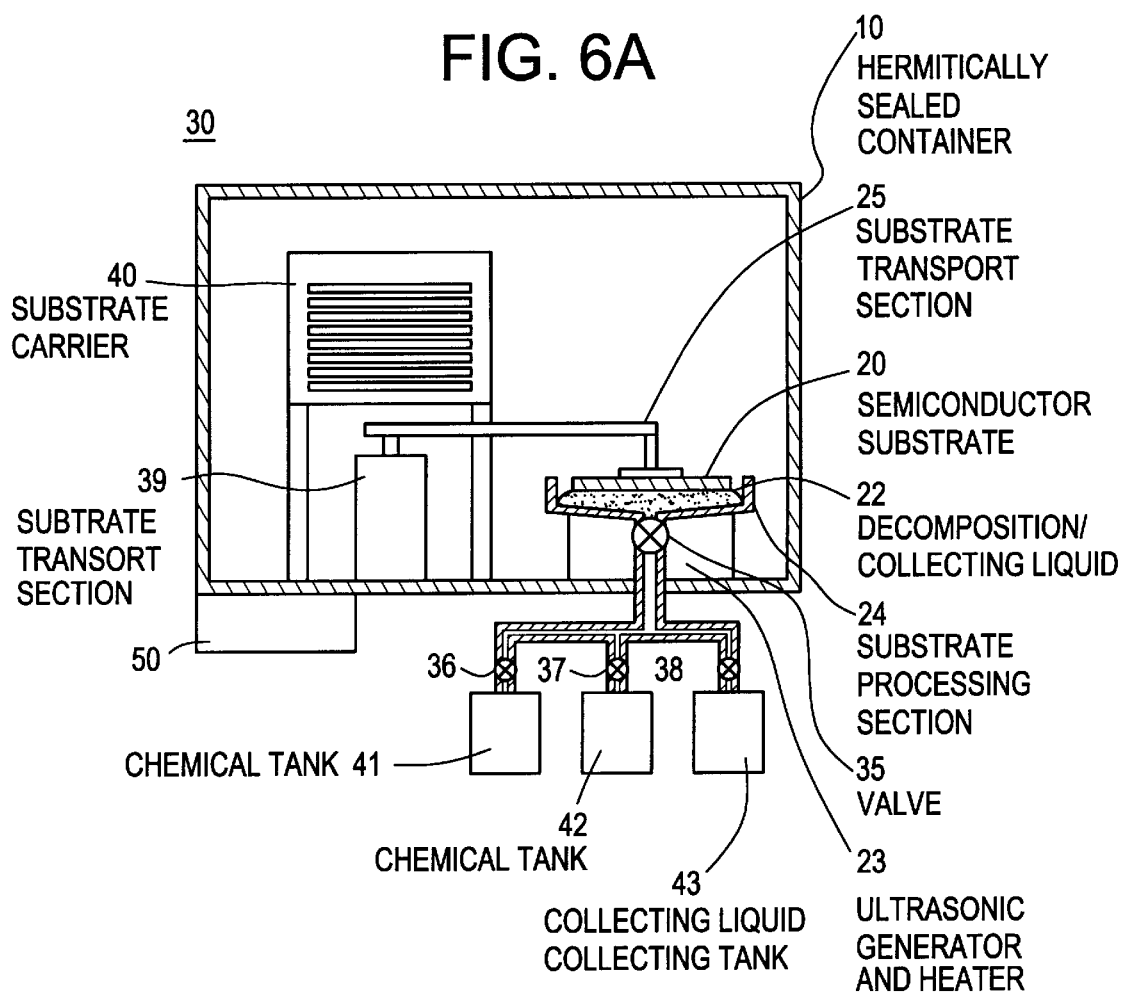
FIG. 6 is a drawing which shows the configuration of yet another example of a semiconductor substrate analysis pre-processing apparatus according to the present invention, FIG. 6(A) showing a side view thereof, and FIG. 6(B) showing a plain view thereof.
Figure 6B:
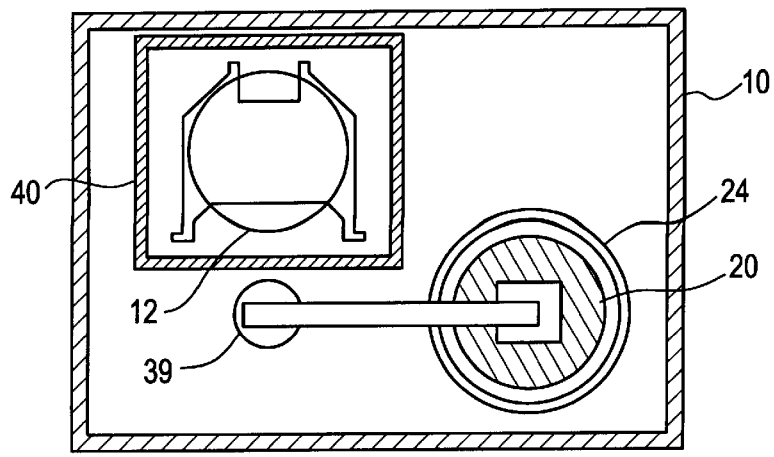
Figure 7:
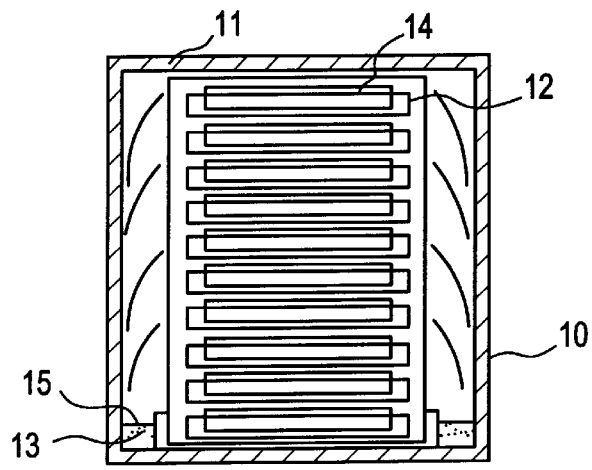
FIG. 7 is a side view that shows a hermetically sealed container for hydrofluoric acid vapor used in a pre-processing method of the past.
Figure 8A:
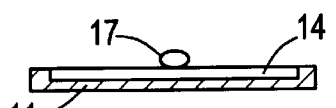
FIG. 8(A) through FIG. 8(E) are side views and plan views which show the operation of decomposition and collecting in a pre-processing method of the past.
Figure 8B:
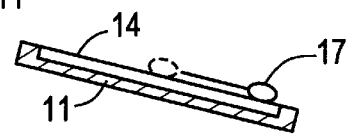
Figure 8C:
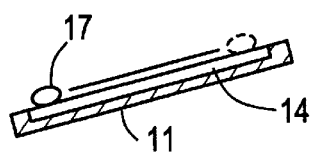
Figure 8D:
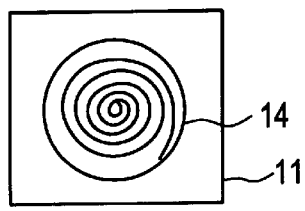
Figure 8E:
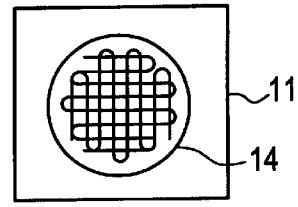
Figure 9A:
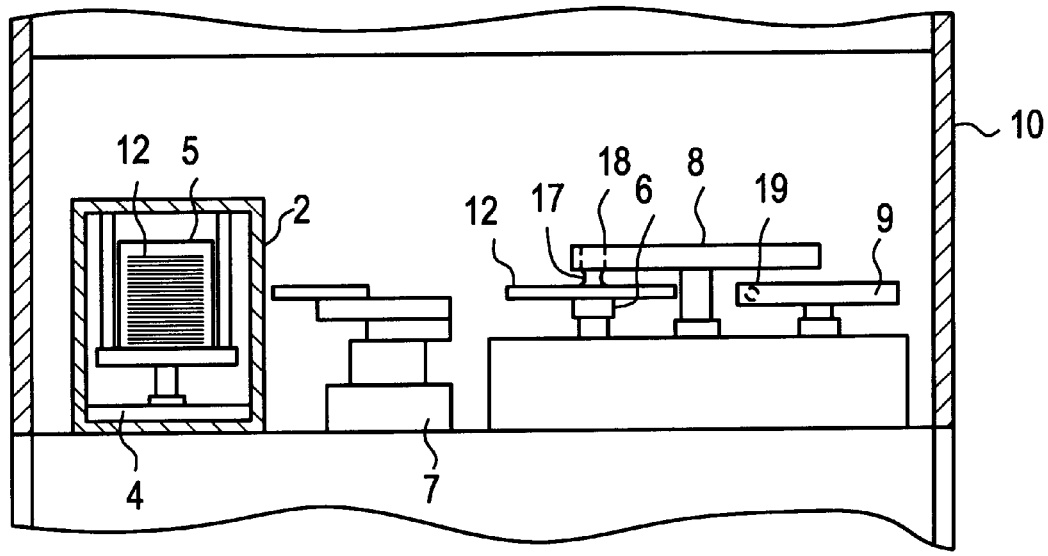
FIG. 9 is a drawing which shows the configuration of an example of an automated pre-processing apparatus of the past, FIG. 9(A) being a side view thereof, and FIG. 9(B) being a plan view thereof.
Figure 9B:
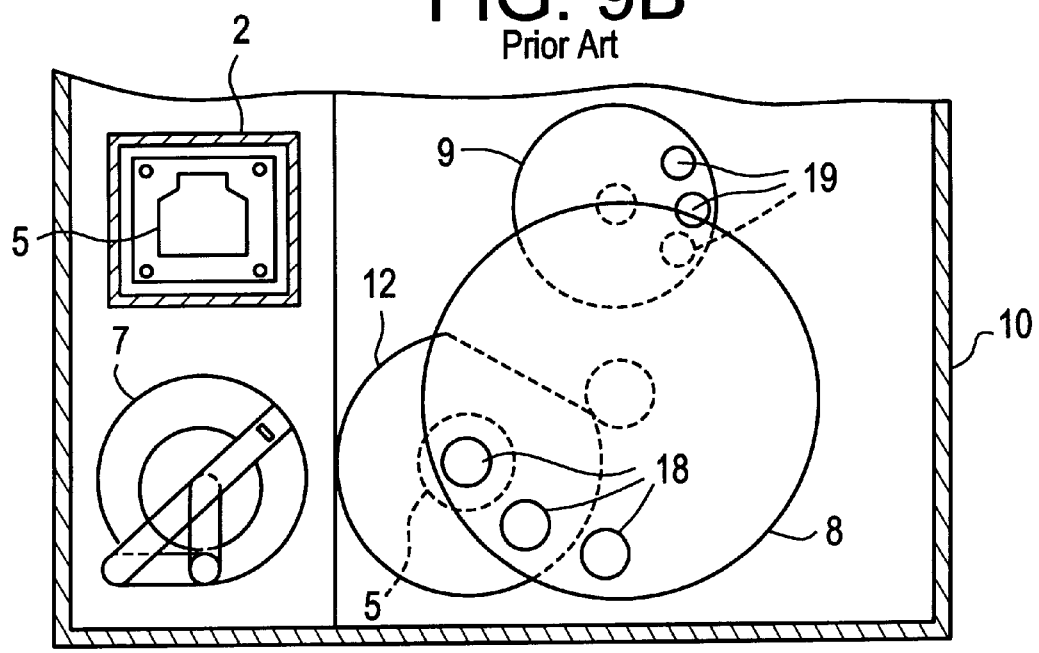

FIG. 6(A) is a side view of a semiconductor substrate surface analysis pre-processing apparatus 3 of the third example of the present invention, while FIG. 6(B) is a plan view thereof.

Specifically, by switching a valve 35, which is provided at the bottom center part of the round substrate processing section 24 made of a fluororesin and which has a slope downward toward the center thereof, the collecting liquid 22 is guided from the collecting liquid tanks 36 and 37.

The collecting liquid tanks 41 and 42 are connected to several bottles which contain various acids, mixing being done to an arbitrary liquidity and concentration when these are guided into the substrate processing section.

The semiconductor substrate 20 is transported from the carrier 40, and, from above the collecting liquid 22 that is guided into the substrate processing section 24, the substrate transport section 25, which is formed by a vacuum chuck or the like, causing the surface of the substrate 20 which it holds to come into horizontal contact, so that its entire surface is immersed into the collecting liquid.

In this condition, ultrasonic or heat processing is performed, thereby decomposing or dissolving the metallic contaminating matter that is attached to the substrate surface, which is then captured in the collecting liquid.

After collecting, the substrate is lifted up by an edge at a low speed, so as to separate it from the collecting liquid.

When doing this, an edge on the other side of the substrate is kept in contact with the collecting liquid, after which that part is lifted up.

Thereafter, the valve is switched so that the collecting liquid is collected into the collecting liquid collecting tank, a concentration measurement being performed on this liquid by means of a high-sensitivity metallic impurity analyzer such as AAS and ICP-MS.

Furthermore, in this example, a control means 50 is provided for overall control of the various means and equipment.

As described above, by using either ultrasonic or heat treating to perform decomposition and collection over the entire surface area of a substrate, the present invention provides an extremely large effect, by improving the reproducibility of the collection rate, shortening the pre-processing time, simplifying the accommodation of various decomposition/collecting liquids, and simplifying the accommodation of semiconductor substrates of further increased size.

Furthermore, because an apparatus according to the present invention is simpler than those of the past, it is possible to achieve a smaller and lower-cost apparatus.

With the present invention, therefore, it is possible to obtain a precise grasp of contamination by metallic elements during semiconductor manufacturing, and an additional effect is that it is possible, by reducing contamination, to achieve a semiconductor product that has high reliability and high production yield.

What is claimed is:

1. A semiconductor substrate surface analysis pre-processing method, comprising the steps of:
   bringing a decomposition/collecting liquid in contact with an entire surface of a substrate to be surface-analyzed to a distance such that said decomposition/collecting liquid does not flow around to the reverse side of the substrate, and
   subjecting said decomposition/collecting liquid to ultrasonic processing or heat treatment.

2. A semiconductor substrate analysis pre-processing method according to claim 1, wherein both ultrasonic processing and heat treatment are performed with respect to said decomposition/collecting liquid.

3. A semiconductor substrate surface analysis pre-processing method according to claim 1, wherein said decomposition/collecting liquid is at least one dilute aqueous solution or dilute mixture of aqueous solutions selected from the group consisting of pure water, hydrofluoric acid, hydrofluoric acid-hydrogen peroxide solution, hydrofluoric acid-nitric acid, hydrochloric acid-hydrogen peroxide solution, ammonia-hydrogen peroxide solution, sulfuric acid-hydrogen peroxide solution, and hydrochloric acid-nitric acid.

4. A semiconductor substrate surface analysis pre-processing method according to claim 3, wherein said decomposition/collecting liquid includes a surfactant.

5. A semiconductor substrate surface analysis pre-processing apparatus which comprises:
   a substrate processing section that supports a decomposition/collecting liquid that is caused to come into contact with the entire surface of a semiconductor substrate with respect to which surface analysis is to be performed;
   a substrate transport section, which supports said substrate to be surface-analyzed, which lowers said substrate into contact with said decomposition/collecting liquid to a distance such that said decomposition/collecting liquid does not flow around to the reverse side and which moves said substrate between a substrate carrier section and said substrate processing section;

a supply and ejection apparatus for said decomposition/collecting fluid; and a processing operation section that subjects said substrate to either ultrasonic or heating processing.

6. A semiconductor substrate surface analysis preprocessing apparatus according to claim 5, wherein at least a part of said substrate processing section which comes into contact with said decomposition/collecting liquid is made of a fluororesin.

7. A semiconductor substrate surface analysis preprocessing apparatus according to claim 5, wherein said substrate processing section includes a function of causing said substrate to be surface-analyzed to come into contact with said decomposition/collecting liquid, and a function of separating said substrate surface from said decomposition/collecting liquid, and also minimally has a function that, when said substrate surface for surface-analysis is removed from said decomposition/collecting liquid, removes said substrate in such a manner that the surface of said decomposition/collecting liquid and contact surface of aid substrate with said decomposition/collecting liquid intersect.

* * * * *